United States Patent
Sarris et al.

(10) Patent No.: US 6,723,338 B1
(45) Date of Patent: Apr. 20, 2004

(54) COMPOSITIONS AND METHODS FOR TREATING LYMPHOMA

(75) Inventors: Andreas H. Sarris, Houston, TX (US); Fernando Cabanillas, Houston, TX (US); Patricia M. Logan, Vancouver (CA); Clive T. R. Burge, Brentwood Bay (CA); James H. Goldie, Vancouver (CA); Murray S. Webb, Delta (CA)

(73) Assignees: Inex Pharmaceuticals Corporation, Burnaby (CA); Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/541,436

(22) Filed: Mar. 31, 2000

Related U.S. Application Data

(60) Provisional application No. 60/137,194, filed on Jun. 2, 1999, and provisional application No. 60/127,444, filed on Apr. 1, 1999.

(51) Int. Cl.[7] ............................................. A61K 9/127
(52) U.S. Cl. ........................................................ 424/450
(58) Field of Search .................................. 424/450, 812; 436/829

(56) References Cited

U.S. PATENT DOCUMENTS

| 4,952,408 A | * | 8/1990 | Rahman ...................... 426/450 |
| 5,165,922 A | * | 11/1992 | Hellstrom .................. 424/85.8 |
| 5,567,592 A | * | 10/1996 | Benet ......................... 435/7.21 |
| 5,595,756 A | * | 1/1997 | Bally .......................... 424/450 |
| 5,741,516 A | * | 4/1998 | Webb .......................... 426/450 |

* cited by examiner

*Primary Examiner*—Collamudi S. Kishore
(74) *Attorney, Agent, or Firm*—Seed Intellectual Property Law Group PLLC

(57) ABSTRACT

This invention provides methods for treating neoplasias in a mammal. In particular, the invention provides methods for treating various types of lymphomas, including relapsed forms of non-Hodgkin's Lymphoma. These methods involve the administration of liposome-encapsulated vinca alkaloids, e.g., vincristine, to a mammal with a lymphoma.

27 Claims, 2 Drawing Sheets

Response to Liposomal Vincristine in Relapsed Aggressive NHL
Effect of Prior Regimen Number

| | 1 Rx | ≥ 2 Rx | ≥ 2, Respond to Last Rx | ≥ 2, Fail Last Rx |
|---|---|---|---|---|
| Evaluable | 11 | 26 | 8 | 18 |
| CR | 4 | - | - | - |
| PR | 4 | 10 | 3 | 7 |
| % Response | 73 | 38 | 38 | 39 |
| 95% Confidence Interval | 39-95 | 20-59 | 9-76 | 17-64 |

Clinical Response Rates

| | Indolent | Transformed | Relapsed Lymphoma | Refractory Aggressive | Aggressive post-BMT |
|---|---|---|---|---|---|
| Evaluable | 18 | 16 | 37 | 11 | 10 |
| CR/PR | 1 | 5 | 18 | 0 | 2 |
| % Response | 6 | 31 | 49 | 0 | 20 |
| 95% Confidence Interval | 0 - 28 | 11 - 59 | 32 - 66 | 0 - 28 | 1 - 32 |

Figure 1

Response to Liposomal Vincristine in Relapsed Aggressive NHL
Effect of Prior Regimen Number

|  | 1 Rx | ≥ 2 Rx | ≥ 2, Respond to Last Rx | ≥ 2, Fail Last Rx |
|---|---|---|---|---|
| Evaluable | 11 | 26 | 8 | 18 |
| CR | 4 | - | - | - |
| PR | 4 | 10 | 3 | 7 |
| % Response | 73 | 38 | 38 | 39 |
| 95% Confidence Interval | 39-95 | 20-59 | 9-76 | 17-64 |

COMPOSITIONS AND METHODS FOR TREATING LYMPHOMA

CROSS-REFERENCE TO RELATED APPLICATION

This patent application claims priority to U.S. Provisional Patent Application Nos. 60/127,444, filed Apr. 1, 1999, and Ser. No. 60/137,194, filed Jun. 2, 1999, each of which is incorporated by reference in its entirety.

FIELD OF THE INVENTION

This invention relates to methods and compositions for treatment of a neoplasia in a mammal, and in particular, relapsed forms of neoplasias.

BACKGROUND OF THE INVENTION

Despite years of research into the development of new methods of treatment, cancers of the lymphatic system, or lymphomas, remain quite common. For example, more than 60,000 people in the United States are diagnosed with lymphoma each year, including more than 55,000 cases of non-Hodgkin's Lymphoma (NHL), and these numbers are constantly increasing. In addition, the prognosis for those affected by these diseases is often poor, as the survival rates for lymphoma patients remain low. Clearly, new methods for treating these diseases are needed.

While traditional treatments for lymphoma typically depend on the type of lymphoma as well as the medical history of the patient, first-line treatment for many lymphomas typically includes chemotherapy. Such chemotherapy will often entail the administration of a "cocktail" of compounds, e.g., the formulation CHOP, which includes cyclophosphamide, doxorubicin, vincristine, and prednisone. In addition, certain first-line cancer treatments also include other forms of cancer therapy, such as radiation therapy.

In many cases, patients respond initially to such first-line treatments, but subsequently suffer a relapse, i.e., a tumor reappears or resumes growing. Following one such relapse, patients are often treated with further chemotherapy, e.g., with CHOP or with other formulations, or, in some cases, the patients are treated with other procedures such as bone marrow transplantation. Again, in many cases, patients initially respond to such additional treatments, but subsequently suffer another relapse. In general, the more relapses a patient suffers, the less agreement there is in the art concerning optimal subsequent treatment. In other cases, a patient fails to respond at all to a treatment, even initially, and is thus said to have a refractory cancer. In such cases as well, little agreement exists in the art regarding optimal subsequent treatment.

Alkaloids isolated from the periwinkle plant (*Vinca rosea*), called "vinca alkaloids," have proven effective for first line treatments of many types of lymphomas, leukemia, and other cancers. One such vinca alkaloid, vincristine, is included in the common chemotherapeutic formulation CHOP. Vincristine, which depolymerizes microtubules and thereby inhibits cell proliferation, is administered in its free form in CHOP. Liposome-encapsulated vincristine has been reported (see, e.g., U.S. Pat. No. 5,741,516, or U.S. Pat. No. 5,714,163). In particular, these patents discuss the use of vincristine encapsulated in phosphatidylcholine, distearoylphosphatidylcholine, or sphingomyelin, in addition to cholesterol. Successful clinical applications of this technology, however, have never been achieved. Indeed, major theoretical and practical uncertainties remain, including uncertainties regarding biodistribution, toxicity, and efficacy.

Lipid-encapsulated drug formulations may provide advantages over traditional drug-delivery methods. For example, some lipid-based formulations provide longer half-lives in vivo, superior tissue targeting, and decreased toxicity. Numerous methods have been described for the formulation of lipid-based drug delivery vehicles (see, e.g., U.S. Pat. No. 5,741,516). No studies, however, have demonstrated that such liposome-encapsulated vinca alkaloid formulations offer any advantages over previous treatments, or have efficacy in the in vivo treatment of cancer in a patient. As such, there remains a need in the art for new methods for treating these diseases. Quite surprisingly, the present invention provides such methods.

SUMMARY OF THE INVENTION

It has now been discovered that liposome-encapsulated vinca alkaloids, such as vincristine, are especially efficacious in first line treatment of neoplasia as well as for the treatment of relapsed forms of neoplasias, in particular for lymphomas such as non-Hodgkin's Lymphomas. Provided herein, therefore, are methods for the treatment of these and other cancers.

In one aspect, this invention provides a method for treating a relapsed cancer in a mammal, the method comprising administering to the mammal a pharmaceutical composition comprising a liposome-encapsulated vinca alkaloid. In one embodiment, the relapsed cancer is a non-Hodgkin's Lymphoma.

In another aspect, the present invention provides a method of treating a non-Hodgkin's Lymphoma in a patient, the method comprising administering to the patient a pharmaceutical composition comprising a liposome-encapsulated vinca alkaloid, wherein the composition is free of cardiolipin.

In one embodiment, the non-Hodgkin's Lymphoma is a member selected from the group consisting of aggressive NHL, transformed NHL, indolent NHL, relapsed NHL, refractory NHL, low grade non-Hodgkin's Lymphoma, follicular lymphoma, large cell lymphoma, B-cell lymphoma, T-cell lymphoma, Mantle cell lymphoma, Burkitt's lymphoma, NK cell lymphoma, diffuse large B-cell lymphoma, and acute lymphoblastic lymphoma.

In one embodiment, the vinca alkaloid is vincristine, vinblastine, vinorelbine, or vindesine. In another embodiment, the liposome comprises distearoylphosphatidylcholine or sphingomyelin. In another embodiment, the liposome further comprises cholesterol. In another embodiment, the liposome comprise a pH gradient. In another embodiment, the pH at the interior of the liposomes is lower than the pH at the exterior.

In another embodiment, the mammal is a human. In another embodiment, the mammal has previously undergone at least one chemotherapy treatment. In another embodiment, the chemotherapy treatment comprised administration of a free-form vinca alkaloid, such as vincristine, vinblastine, vindesine, or vinorelbine. In other embodiments, the chemotherapy treatment included an anthracycline-containing combination therapy. In one such embodiment, the anthracycline was doxorubicin. In another embodiment, the mammal has exhibited a partial or complete response to the chemotherapy prior to a relapse of the cancer. In another embodiment, the relapse is a second relapse.

In another embodiment, the liposome-encapsulated vinca alkaloid is administered systemically by intravenous delivery. In another embodiment, the liposome-encapsulated vincristine is co-administered with cyclophosphamide, doxorubicin, and prednisone, forming CHOP (or, in this case, "lipo-CHOP"). In another embodiment, the liposome-encapsulated vinca alkaloid is co-administered with at least one additional anti-tumor agent. In another embodiment, the additional anti-tumor agent is an anti-tumor monoclonal antibody, such as Oncolym™, Rituxan™, or Bexxar™. In another embodiment, the additional anti-tumor agent is an antisense drugs or an anti-tumor vaccine. In another embodiment, the liposome-encapsulated vinca alkaloid is co-administered with a prophylactic or therapeutic treatment for neurotoxicity, such as Neurontin™ gabapentin (Neurotonin).

In another embodiment, the liposome-encapsulated vinca alkaloid is administered to the mammal once every 7–21 days, preferably every 14 days. In another embodiment, the liposome encapsulated vinca alkaloid is administered at a dosage falling within a range of about 1.4 to about 2.4 mg/m$^2$.

The present invention provides an improvement on conventional methods of treating cancer. In particular, the present invention provides a method for treating an aggressive, relapsed, transformed, indolent, or refractory lymphoma in a mammal, the improvement comprising administering a liposome-encapsulated vinca alkaloid such as vincristine (or other liposome-encapsulated therapeutic agent) to the mammal. In addition, the present invention provides a basis for an improved combination chemotherapy for use in first-line treatment of non-Hodgkin's Lymphoma.

Kits including the herein-described formulations, and for preparing the herein-described formulations, as well as instructions for their use are also included.

The present invention also provides the use of a liposome-encapsulated vinca alkaloid in the preparation of a medicament for the treatment of a neoplasia, including non-Hodgkin's Lymphoma. In certain uses, the neoplasia is a relapsed, indolent, aggressive, or transformed neoplasia, e.g., non-Hodgkin's Lymphoma. In other uses, the medicament is used as a first line treatment for a neoplasia. In preferred uses, the vinca alkaloid is vincristine. In other preferred uses, the vinca alkaloid is present in the medicament at a dosage, e.g., of about 2.4 to about 3.4 mg/m$^2$, and is administered once every 7–21 days, most preferably every 14 days.

DEFINITIONS

"Neoplasia," as used herein, refers to any aberrant growth of cells, tumors, malignant effusions, warts, polyps, nonsolid tumors, cysts and other growths. A site of neoplasia can contain a variety of cell types, including but not limited to, neoplastic cells, vascular endothelia, or immune system cells, such as macrophages and leukocytes, etc.

A "cancer" in a mammal refers to any of a number of conditions caused by the abnormal, uncontrolled growth of cells. Cells capable of causing cancer, called "cancer cells", possess a number of characteristic properties such as uncontrolled proliferation, immortality, metastatic potential, rapid growth and proliferation rate, and certain typical morphological features. Often, cancer cells will be in the form of a tumor, but such cells may also exist alone within a mammal, or may be a non-tumorigenic cancer cell, such as a leukemia cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, AFP, HCG, CA 19-9, CA 15-3, CA 27-29, LDH, NSE, and others), and detecting a genotype indicative of a cancer (e.g., TP53, ATM, etc.). However, a negative result in one or more of the above detection methods does not necessarily indicate the absence of cancer, e.g., a patient who has exhibited a complete response to a cancer treatment may still have a cancer, as evidenced by a subsequent relapse.

"Systemic delivery," as used herein, refers to delivery that leads to a broad bio-distribution of a compound within an organism. Systemic delivery means that a useful, preferably therapeutic, amount of a compound is exposed to most parts of the body. To obtain broad bio-distribution generally requires a route of introduction such that the compound is not rapidly degraded or cleared (such as by first pass organs (liver, lung, etc.) or by rapid, nonspecific cell binding) before reaching a disease site. Systemic delivery of liposome-encapsulated vinca alkaloids is preferably obtained by intravenous delivery.

"Lymphoma" refers to a malignant growth of B or T cells in the lymphatic system. "Lymphoma" includes numerous types of malignant growths, including Hodgkin's Lymphoma and non-Hodgkin's lymphoma (NHL). "Non-Hodgkin's Lymphoma" refers to a malignant growth of B or T cells in the lymphatic system that is not a Hodgkin's Lymphoma (which is characterized, e.g., by the presence of Reed-Sternberg cells in the cancerous area). Non-Hodgkin's lymphomas encompass over 29 types of lymphoma, the distinctions between which are based on the type of cancer cells. The particular classification depends on the particular system of classification used, such as the Working formulation, the Rappaport classification, and the REAL classification. In preferred embodiments, the REAL classification is used.

A "relapsed cancer" or lymphoma refers to a cancer or lymphoma that has recurred following prior complete or partial remission in response to a prior treatment. Recurrence can be defined in any way, including a reappearance or re-growth of a tumor as detected by clinical, radiological, or biochemical assays, or by an increased level of a cancer marker. Prior treatments can include, but are not limited to, chemotherapy, radiation therapy, and bone marrow transplantation.

An "indolent" non-Hodgkin's Lymphoma is a classification that includes slow growing forms of lymphoma. They encompass what are called low grade and some categories of intermediate grade NHL in the Working Formulation. Indolent NHLs are sometimes not responsive to conventional cancer therapies such as chemotherapy and radiation therapy.

A "transformed" non-Hodgkin's Lymphoma is a classification sometimes employed to describe an indolent NHL which acquires an aggressive aspect and becomes more responsive to standard chemotherapies.

Patients with "refractory cancer" or "refractory lymphoma" are those who have failed to achieve complete remission on their first course of combination chemotherapy, or to patients who have failed to achieve complete or partial remission on subsequent chemotherapy. "Primary refractory" patients are those who have never achieved complete remission even at first treatment.

A "stable disease" is a state wherein a therapy causes cessation of growth or prevalence of a tumor or tumors as measured by the usual clinical, radiological and biochemical means, although there is no regression or decrease in the size or prevalence of the tumor or tumors, i.e., cancer that is not decreasing or increasing in extent or severity.

"Partial response" or "partial remission" refers to the amelioration of a cancerous state, as measured by tumor size and/or cancer marker levels, in response to a treatment. Typically, a "partial response" means that a tumor or tumor-indicating blood marker has decreased in size or level by about 50% in response to a treatment. The treatment can be any treatment directed against cancer, but typically includes chemotherapy, radiation therapy, hormone therapy, surgery, cell or bone marrow transplantation, immunotherapy, and others. The size of a tumor can be detected by clinical or by radiological means. Tumor-indicating markers can be detected by means well known to those of skill, e.g., ELISA or other antibody-based tests.

A "complete response" or "complete remission" means that a cancerous state, as measured by, for example, tumor size and/or cancer marker levels, has disappeared following a treatment such as chemotherapy, radiation therapy, hormone therapy, surgery, cell or bone marrow transplantation, or immunotherapy. The presence of a tumor can be detected by clinical or by radiological means. Tumor-indicating markers can be detected by means well known to those of skill, e.g., ELISA or other antibody-based tests. A "complete response" does not necessarily indicate that the cancer has been cured, however, as a complete response can be followed by a relapse.

"Chemotherapy" refers to the administration of chemical agents that inhibit the growth, proliferation and/or survival of cancer cells. Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapy can include any chemical agent that inhibits, or is designed to inhibit, a cancerous cell or a cell likely to become cancerous. Such agents are often administered, and are often most effective, in combination, e.g., in the formulation CHOP.

"Radiation therapy" refers to the administration of radioactivity to an animal with cancer. Radiation kills or inhibits the growth of dividing cells, such as cancer cells.

"Surgery" is the direct removal or ablation of cells, e.g., cancer cells, from an animal. Most often, the cancer cells will be in the form of a tumor (e.g., resulting from a lymphoma), which is removed from the animal.

"Hormone therapy" refers to the administration of compounds that counteract or inhibit hormones, such as estrogen or androgen, that have a mitogenic effect on cells. Often, these hormones act to increase the cancerous properties of cancer cells in vivo.

"Immunotherapy" refers to methods of enhancing the ability of an animal's immune system to destroy cancer cells within the animal.

A "free-form" therapeutic agent, or "free" therapeutic agent, refers to a therapeutic agent that is not liposome-encapsulated. Usually, a drug is presumed to be "free, or in a "free-form," unless specified otherwise. A vinca alkaloid in free form may still be present in combination with other reagents, however, such as other chemotherapeutic compounds, a pharmaceutical carrier, or complexing agents, i.e. as used herein the term only specifically excludes lipid formulations of the vinca alkaloids.

BRIEF DESCRIPTION OF THE DRAWINGS

FIG. 1 provides results for a clinical trial using the herein-described methods, in particular regarding the efficacy of the methods in the treatment of indolent, transformed, relapsed, and aggressive post bone-marrow transplant (BMT) forms of non-Hodgkin's Lymphoma.

FIG. 2 provides results concerning the response to liposomal vincristine in Relapsed Aggressive NHL, particularly with regard to the effect of the prior regimen number.

DETAILED DESCRIPTION OF THE INVENTION AND PREFERRED EMBODIMENTS

This invention provides methods of treating neoplasia in a patient. This invention is based on the discovery that liposome-encapsulated vinca alkaloids are unusually effective in the treatment of a variety of forms of lymphoma. In particular, the surprising discovery was made that the administration of liposome-encapsulated vinca alkaloids increases the median survival of patients with lymphoma. In a particularly preferred embodiment, vincristine, encapsulated in a sphingomyelin and cholesterol based liposome, is used in the treatment of non-Hodgkin's Lymphoma, especially relapsed forms of non-Hodgkin's Lymphoma (NHL). The invention also provides, inter alia, methods of treating indolent, transformed, and aggressive forms of NHL.

Often, such treatments of relapsed, indolent, transformed, and aggressive forms of non-Hodgkin's Lymphoma are administered following at least one course of a primary anti-cancer treatment, such as chemotherapy and/or radiation therapy, followed by at least one partial or complete response to the at least one treatment. In other embodiments, the liposomal vinca alkaloids are administered as a first line treatment. In any of these embodiments, the liposome-encapsulated vinca alkaloids can be provided as a single agent or in a combination therapy.

The present invention further provides dosages and dose scheduling of liposomal vinca alkaloids for treatment of solid and non-solid tumors with reduced toxicity.

I. Cancers Treatable with Lipid-Encapsulated Vinca Alkaloids

The methods described herein can be used to treat any type of cancer. In particular, these methods can be applied to cancers of the blood and lymphatic systems, including lymphomas, leukemia, and myelomas.

In preferred embodiments, the present methods are used to treat any of the large number of lymphomas. For example, both Hodgkin's and non-Hodgkin's Lymphomas can be treated using the methods described herein. In particularly preferred embodiments, the methods are used to treat non-Hodgkin's Lymphoma (NHL), including any type of NHL as defined according to any of the various classification systems such as the Working formulation, the Rappaport classification and, preferably, the REAL classification. Such lymphomas include, but are not limited to, low-grade, intermediate-grade, and high-grade lymphomas, as well as both B-cell and T-cell lymphomas. Included in these categories are the various types of small cell, large cell, cleaved cell, lymphocytic, follicular, diffuse, Burkitt's, Mantle cell, NK cell, CNS, AIDS-related, lymphoblastic, adult lymphoblastic, indolent, aggressive, transformed and other types of lymphomas. The methods of the present invention can be used for adult or childhood forms of lymphoma, as well as lymphomas at any stage, e.g., stage I, II, III, or IV. The various types of lymphomas are well known to those of skill, and are described, e.g., by the American Cancer Society (see, e.g., www3.cancer.org).

The methods described herein are also preferably applied to any form of leukemia, including adult and childhood forms of the disease. For example, any acute, chronic, myelogenous, and lymphocytic form of the disease can be treated using the methods of the present invention. In preferred embodiments, the methods are used to treat Acute Lymphocytic Leukemia (ALL). More information about the various types of leukemia can be found, inter alia, from the Leukemia Society of America (see, e.g., www.leukemia.org).

Additional types of tumors can also be treated using the methods described herein, such as neuroblastomas, myelomas, prostate cancers, small cell lung cancer, and others.

II. First-Line Treatments

In numerous embodiments of the present invention, liposome-encapsulated vinca alkaloids will be used as a first-line treatment for cancer. In preferred embodiments, liposome-encapsulated vinca alkaloids are used to treat lymphoma, particularly non-Hodgkin's Lymphoma. As used herein, "first-line treatment" refers to a primary treatment for a patient presenting with a cancer, in contrast to a relapsed or refractory cancer.

In such embodiments, the liposome-encapsulated vinca alkaloids can be used alone or, preferably, in combination with other chemotherapeutic agents, such as cyclophosphamide, doxorubicin, and prednisone. Particularly preferred is the use of liposome encapsulated vincristine along with cyclophosphamide, doxorubicin, and prednisone, thereby forming an improved, liposomal CHOP formulation ("lipo-CHOP.")

When used as a single agent in first-line treatment, dosages and dose scheduling is preferably the same as single agent treatment for relapsed cancer. When used in combination regimes, dosages and dose scheduling may be revised to correspond to the preferred regimen for the combination.

III. Relapsed or Refractory Forms of the Diseases

The present methods can be used to treat primary, relapsed, transformed, or refractory forms of cancer. Often, patients with relapsed cancers have undergone one or more treatments including chemotherapy, radiation therapy, bone marrow transplants, hormone therapy, surgery, and the like. Of the patients who respond to such treatments, they may exhibit stable disease, a partial response (i.e., the tumor or a cancer marker level diminishes by at least 50%), or a complete response (i.e., the tumor as well as markers become undetectable). In either of these scenarios, the cancer may subsequently reappear, signifying a relapse of the cancer.

In certain embodiments, the methods provided herein will be used to treat a patient that has undergone a single course of treatment for a cancer, has partially or completely responded to such treatment, and has subsequently suffered a relapse. In other embodiments, patients are treated who have undergone more than one course of treatment, have responded more than once, and have subsequently suffered more than one relapse. The previous course of treatment can include any anti-cancer treatment, including chemotherapy, radiation therapy, bone marrow transplant, etc.

In certain embodiments of the present invention, liposomal alkaloids are employed against "resistant" cancers, i.e., cancers which have previously exhibited a complete response to a treatment, but which subsequently manifest a resistance to second or later course of treatment.

IV. Vinca and Other Alkaloids

The present invention can include the use of any naturally occurring alkaloid, including vinca alkaloids, or any synthetic derivative of a naturally occurring alkaloid. Vinca alkaloids include, but are not limited to, vinblastine, vincristine, vindoline, vindesine, vinleuro sine, vinrosi dine, vinorelbine, or derivatives thereof (see, e.g., the Merck Index, 11$^{th}$ Edition (1989) entries 9887,989 1, and 9893, for vinblastine, vincristine, and vindoline). Examples of other suitable alkaloids include, but are not limited to, the podophyllins, podophyllotoxins, and derivatives thereof (e.g., etoposide, etoposide phosphate, teniposide, etc.), the camptothecins (e.g., irinotecan, topotecan, etc.) the taxanes (taxol, etc.), and derivatives thereof. All of the above compounds are well known to those of skill and are readily available from commercial sources, by synthesis, or by purification from natural sources.

In preferred embodiments, the vinca alkaloid used in the present invention is vincristine. Vincristine, also known as leurocristine sulfate, 22-oxovincaleukoblastine, Kyocristine, vincosid, vincrex, oncovin, Vincasar PFS®, or VCR, is commercially available from any of a number of sources, e.g., Pharmacia & Upjohn, Lilly, IGT, etc. It is often supplied as vincristine sulfate, e.g., as a 1 mg/mL solution.

The present invention can comprise the use of a single vinca alkaloid or multiple, co-administered vinca alkaloids. In addition, the one or more vinca alkaloids can be combined with other compounds or molecules, such as other antineoplastic agents. In certain embodiments, such combinations of vinca alkaloids and/or other compounds can be made prior to liposomal formulation, thereby creating a combination within a single liposome. In other embodiments, liposome-encapsulated vinca alkaloids are formulated and subsequently combined with the other molecules, which can themselves be free-form or liposome-encapsulated.

Any of the therapeutic agents described herein, including liposome-encapsulated alkaloids, can be subjected to pre-clinical testing in well known models of human diseases. In vivo models of human lymphoma include mice carrying the non-Hodgkin's B-cell line DoHH2 (Kluin-Nelemans HC, et al. (1991) Leukemia 5(3) 221–224), or mice carrying Daudi or Raji cell xenografts (see, for example Hudson, WA et al. (1998) Leukemia 12(12): 2029–2033). Many other oncological models can also be used and are known to those skilled in the art.

V. Lipids

Any of a number of lipids can be used to prepare the liposomes of the present invention, including amphipathic, neutral, cationic, and anionic lipids. Such lipids can be used alone or in combination, and can also include bilayer stabilizing components such as polyamide oligomers (see, e.g., U.S. Patent application "Polyamide Oligomers", by Ansell, U.S. application Ser. No. 09/218,988, filed Dec. 22, 1998), peptides, proteins, detergents, lipid-derivatives, such as PEG coupled to phosphatidylethanolamine and PEG conjugated to ceramides (see, U.S. application Ser. No. 08/485,608). In a preferred embodiment, cloaking agents, which reduce elimination of liposomes by the host immune system, can also be included, such as polyamide-oligomer conjugates, e.g., ATTA-lipids, (see, U.S. patent application Ser. No. 08/996,783, filed Feb. 2, 1998) and PEG-lipid conjugates (see, U.S. patent application Ser. Nos. 08/486,214, 08/316, 407 and 08/485,608).

Any of a number of neutral lipids can be included, referring to any of a number of lipid species which exist either in an uncharged or neutral zwitterionic form at physiological pH, including diacylphosphatidylcholine, diacylphosphatidylethanolamine, ceramide, sphingomyelin, cephalin, cholesterol, cerebrosides, and diacylglycerols.

In preferred embodiments, the lipid used is sphingomyelin. In particularly preferred embodiments, the lipid comprises sphingomyelin and cholesterol. In such embodiments, the ratio of sphingomyelin to cholesterol is typically between about 75/25 (mol % sphingomyelin/mol % cholesterol) and about 50/50 (mol % sphingomyelin/mol % cholesterol), preferably between about 70/30 and 55/45 (mol % sphingomyelin/mol % cholesterol), and most preferably about 55/45 (mol % sphingomyelin/mol % cholesterol). Such ratios, may be altered, however, by the addition of other lipids into the present formulations.

Cationic lipids, which carry a net positive charge at physiological pH, can readily be incorporated into liposomes for use in the present invention. Such lipids include, but are not limited to, N,N-dioleyl-N,N-dimethylammonium chloride ("DODAC"); N-(2,3-dioleyloxy)propyl-N,N-N-triethylammonium chloride ("DOTMA"); N,N-distearyl-N, N-dimethylammonium bromide ("DDAB"); N-(2,3-dioleoyloxy)propyl)-N,N,N-trimethylammonium chloride ("DOTAP"); 3β-(N-(N',N'-dimethylaminoethane)-carbamoyl)cholesterol ("DC-Chol"), N-(1-(2,3-dioleyloxy)propyl)-N-2-(sperminecarboxamido)ethyl)-N,N-dimethylammonium trifluoracetate ("DOSPA"), dioctadecylamidoglycyl carboxyspermine ("DOGS"), 1,2-dileoyl-sn-3-phosphoethanolamine ("DOPE"); and N-(1,2-dimyristyloxyprop-3-yl)-N,N-dimethyl-N-hydroxyethyl ammonium bromide ("DMRIE"). Additionally, a number of commercial preparations of cationic lipids can be used, such as LIPOFECTIN (including DOTMA and DOPE, available from GIBCO/BRL), LIPOFECTAMINE (comprising DOSPA and DOPE, available from GIBCO/BRL), and TRANSFECTAM (comprising DOGS, in ethanol, from Promega Corp.).

Anionic lipids suitable for use in the present invention include, but are not limited to, phosphatidylglycerol, cardiolipin, diacylphosphatidylcholine, diacylphosphatidic acid, N-dodecanoyl phosphatidylethanolamine, N-succinyl phosphatidylethanolamine, N-glutaryl phosphatidylethanolamine, lysylphosphatidylglycerol, and other anionic modifying groups joined to neutral lipids.

In numerous embodiments, amphipathic lipids will be used. "Amphipathic lipids" refer to any suitable material, wherein the hydrophobic portion of the lipid material orients into a hydrophobic phase, while the hydrophilic portion orients toward the aqueous phase. Such compounds include, but are not limited to, phospholipids, aminolipids, and sphingolipids. Representative phospholipids include sphingomyelin, phosphatidylcholine, phosphatidylethanolamine, phosphatidylserine, phosphatidylinositol, phosphatidic acid, palmitoyloleoyl phosphatdylcholine, lysophosphatidylcholine, lysophosphatidylethanolamine, dipalmitoylphosphatidylcholine, dioleoylphosphatidylcholine, distearoylphosphatidylcholine, or dilinoleoylphosphatidylcholine. Other phosphorus-lacking compounds, such as sphingolipids, glycosphingolipid families, diacylglycerols, and β-acyloxyacids, can also be used. Additionally, such amphipathic lipids can be readily mixed with other lipids, such as triglycerides and sterols.

The liposomes used in the present invention can be multilamellar or unilamellar, which can be formed using the methods disclosed herein and other methods known to those of skill in the art.

Also suitable for inclusion in the present invention are programmable fusion lipid formulations. Such formulations have little tendency to fuse with cell membranes and deliver their payload until a given signal event occurs. This allows the lipid formulation to distribute more evenly after injection into an organism or disease site before it starts fusing with cells. The signal event can be, for example, a change in pH, temperature, ionic environment, or time. In the latter case, a fusion delaying or "cloaking" component, such as an ATTA-lipid conjugate or a PEG-lipid conjugate, can simply exchange out of the liposome membrane over time. By the time the formulation is suitably distributed in the body, it has lost sufficient cloaking agent so as to be fusogenic. With other signal events, its is desirable to choose a signal that is associated with the disease site or target cell, such as increased temperature at a site of inflammation.

VI. Making Liposomes

A variety of methods are available for preparing liposomes as described in, e.g., Szoka, et al., *Ann. Rev. Biophys. Bioeng.*, 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta*, 443:629–634 (1976); Fraley, et al., *Proc. Natl. Acad. Sci. USA*, 76:3348–3352 (1979); Hope, et al., *Biochim. Biophys. Acta*, 812:55–65 (1985); Mayer, et al., *Biochim. Biophys. Acta*, 858:161–168 (1986); Williams, et al., *Proc. Natl. Acad. Sci.*, 85:242–246 (1988), the text Liposomes, Marc J. Ostro, ed., Marcel Dekker, Inc., New York, 1983, Chapter 1, and Hope, et al., *Chem. Phys. Lip.*, 40:89 (1986), all of which are incorporated herein by reference. Suitable methods include, but are not limited to, sonication, extrusion, high pressure/homogenization, microfluidization, detergent dialysis, calcium-induced fusion of small liposome vesicles, and ether-infusion methods, all of which are well known in the art.

One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents, such as deoxycholate.

Unilamellar vesicles can be prepared by sonication or extrusion. Sonication is generally performed with a tip sonifier, such as a Branson tip sonifier, in an ice bath. Typically, the suspension is subjected to severed sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester, Mass. Unilamellar vesicles can also be made by dissolving phospholipids in ethanol and then injecting the lipids into a buffer, causing the lipids to spontaneously form unilamellar vesicles. Also, phospholipids can be solubilized into a detergent, e.g., cholates, Triton X, or n-alkylglucosides. Following the addition of the drug to the solubilized lipid-detergent micelles, the detergent is removed by any of a number of possible methods including dialysis, gel filtration, affinity chromatography, centrifugation, and ultrafiltration.

Following liposome preparation, the liposomes which have not been sized during formation may be sized to achieve a desired size range and relatively narrow distribution of liposome sizes. A size range of about 0.2–0.4 microns allows the liposome suspension to be sterilized by filtration through a conventional filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method that relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, $Ann.\ Rev.\ Biophys.\ Bioeng.$, 10:421–450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. For use in the present invention, liposomes having a size ranging from about 0.05 microns to about 0.40 microns are preferred. In particularly preferred embodiments, liposomes are between about 0.05 and about 0.2 microns.

In preferred embodiments, empty liposomes are prepared using conventional methods known to those of skill in the art.

Typically, as discussed infra, the liposomes used in the present invention will comprise a transmembrane potential, whereby antineoplastic agents such as vinca alkaloids are effectively loaded into and retained by the liposome. In preferred embodiments, the potential will be effected by creating a pH gradient across the membrane. In particularly preferred embodiments, the pH is lower at the interior of the liposomes than at the exterior. Such gradients can be achieved, e.g., by formulating the liposomes in the presence of a buffer with a low pH, e.g., having a pH between about 2 and about 6, and subsequently transferring the liposomes to a higher pH solution. In preferred embodiments, the pH is between about 3 and 5, and in most preferred embodiments, the pH is about 4. Any of a number of buffers can be used, such as citrate.

Subsequently, before or after sizing, the external pH can be raised, e.g., to about 7 or 7.5, by the addition of a suitable buffer, such as a sodium phosphate buffer. Raising the external pH creates a pH gradient across the liposomal membrane, thereby promoting efficient drug loading and retention.

Liposomes prepared according to these methods can be stored for substantial periods of time prior to drug loading and administration to a patient. For example, liposomes can be dehydrated, stored, and subsequently rehydrated, loaded with one or more vinca alkaloids, and administered. Dehydration can be accomplished, e.g., using standard freeze-drying apparatus, i.e., they are dehydrated under low pressure conditions. Also, the liposomes can be frozen, e.g., in liquid nitrogen, prior to dehydration. Sugars can be added to the liposomal environment, e.g., to the buffer containing the liposomes, prior to dehydration, thereby promoting the integrity of the liposome during dehydration. See, e.g., U.S. Pat. No. 5,077,056 or 5,736,155.

In numerous embodiments, the empty liposomes are first formulated in low pH buffer, and then manipulated in one of a variety of ways to obtain liposomes of the desired size. Methods for sizing liposomes include sonication, by bath or by probe, or homogenization. Preferably, following such treatments, the liposomes are between about 0.05 to 0.45 microns. Most preferably, the liposomes are between about 0.05 and about 0.2 microns. Such sized liposomes can then be sterilized by filtration. Also, particle size distribution can be monitored by conventional laser-beam particle size discrimination or the like. In addition, methods of reducing liposome sizes to a relatively well defined size distribution are known, e.g., one or more cycles of extrusion of the liposomes through a small-pore polycarbonate membrane or an asymmetric ceramic membrane.

VII. Preparation of Liposome-Encapsulated Vinca Alkaloids

Any of a number of methods can be used to load the vinca alkaloids and/or other drugs into the liposomes. Such methods include, e.g., an encapsulation technique and a transmembrane potential loading method. Generally, following such methods, the vinca alkaloids are present at about 0.1 mg/mL to about 0.5 mg/mL. Preferably, the vinca alkaloids are present at about 0.15 to 0.2 mg/mL.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. The resulting liposomes encompassing the vinca alkaloids can then be sized as described above.

Transmembrane potential loading has been described in detail in U.S. Pat. Nos. 4,885,172; 5,059,421; 5,171,578; and 5,837,282 (which teaches ionophore loading), each of which is incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., $Na^+$, $K^+$, and/or $H^+$) across the membranes. This concentration gradient is generated by producing liposomes having different internal and external media and has an associated proton gradient. Drug accumulation can then occur in a manner predicted by the Henderson-Hasselbach equation.

Preferred methods of preparing liposome-encapsulated vinca alkaloids for use in the present invention are discussed, e.g., in U.S. Pat. No. Nos. 5,741,516, 5,814,335 and 5,543,152, each of which is assigned to Inex Pharmaceuticals Corp. and is incorporated herein by reference. In a preferred embodiment, liposomal vinca alkaloids are prepared prior to use from a kit including 3 or more vials. At least one of the vials contains a vincristine solution containing, e.g., 1 mg/mL, 2 mg/mL, or 5 mg/mL vincristine sulfate in buffer containing, e.g., 100 or 200 mg/mL mannitol (obtainable from, e.g., SP Pharmaceuticals LLC, Albuquerque, N.Mex.; other excipients that are pharmaceutically acceptable, and in which vincristine remains stable for extended periods, can also be used) and sodium acetate adjusted to pH 3.5 to 5.5, or preferably pH 4.5 to pH 4.7. One of the vials contains a solution containing liposomes comprising sphingomyelin and cholesterol (each of which is commercially available, e.g., from NEN Life Sciences, Avanti Polar Lipids, etc.) and suspended in a 300 mM citrate buffer at, e.g., pH 4.0. Another vial or vials contains a alkaline phosphate buffer (e.g., pH 9.0) such as dibasic sodium phosphate, 14.2 mg/ml (20 ml/vial).

In other preferred embodiments, a kit is used that contains 2 vials containing components that can be used to formulate the claimed liposome-encapsulated vincristine, or a kit containing 1 vial containing a stable preparation of liposomes comprising pre-loaded vincristine. Such stable preparations can be accomplished in any of a number of ways, including, but not limited to, (1) a hydrated preparation stored at ambient temperatures or refrigerated and which contains one or more modifications or components to enhance chemical stability, e.g., antioxidants; (2) a hydrated preparation that was frozen and which includes a suitable excipient to protect from freeze/thaw-induced damage; or (3) a lyophilized preparation. Typically, any of the above-described kits also contain instructions for use as well as clean-up disposal materials.

To prepare the liposomes, the vincristine sulfate and liposome solutions are each added to a sterile vial and mixed, at an appropriate concentration ratio, e.g., 0.01/1.0 to 0.2/1.0 (wt. vinca alkaloid/wt. lipid). The mixture is mixed, e.g., by inverting the vial multiple times. Following the formation of the liposomes in low pH buffer, and either before or after the sizing of the liposomes, the liposomes are introduced into buffer of a higher pH, e.g., a sodium phosphate buffer, thereby creating a pH gradient across the liposome surface. In preferred embodiments, the external environment of the liposomes is between about pH 7.0 and about pH 7.5. The liposomes and vinca alkaloids can be mixed for an amount of time sufficient to achieve the desired alkaloid/lipid ratio. The mixture can be mixed, e.g., by multiple inversions, and heated to temperatures between about 55° C. and about 80° C., preferably between about 60° C. and about 65° C., for about 5, 10, or more minutes. Such treatment causes greater than about 90% of the vincristine to become entrapped within the liposome.

In other embodiments, these steps are followed at a larger scale, and loaded liposomal vincristine is supplied to, e.g., a hospital pharmacy in ready-to-administer format. Such larger scale formulations may be prepared from different starting materials than those described for the kit; in particular, the buffers may be different.

VIII. Targeting Liposomes

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. No. Nos. 4,957,773 and 4,603,044, the teachings of which are incorporated herein by reference). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. The liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposomal surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337–16342 (1990) and Leonetti, et al., *Proc. Natl. Acad. Sci.* (USA), 87:2448–2451 (1990). Other examples of antibody conjugation are disclosed in U.S. patent application Ser. No. 08/316,394, filed Sep. 30, 1994, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds (see, Heath, *Covalent Attachment of Proteins to Liposomes*, 149 *Methods in Enzymology* 111–119 (Academic Press, Inc. 1987)). Other targeting methods include the biotin-avidin system.

IX. Administration of Lipid-Encapsulated Vinca Alkaloids

Liposome-encapsulated vinca alkaloids can be administered in any of a number of ways, including parenteral, intravenous, systemic, local, intratumoral, intramuscular, subcutaneous, intraperitoneal, inhalation, or any such method of delivery. In preferred embodiments, the pharmaceutical compositions are administered Fintravenously by injection. In one embodiment, a patient is given an intravenous infusion of the liposome-encapsulated vinca alkaloids (single agent) through a running intravenous line over, e.g., 30 minutes, 60 minutes, 90 minutes, or longer. In preferred embodiments, a 60 minute infusion is used. Such infusions can be given periodically, e.g., once every 1, 3, 5, 7, 10, 14, 21, or 28 days or longer, preferably once every 7–21 days, and most preferably once every 14 days. As used herein, each administration of a liposomal vinca alkaloid is considered one "course" of treatment.

Suitable formulation for use in the present invention can be found, e.g., in *Remington's Pharmaceutical Sciences*, Mack Publishing Company, Philadelphia, Pa., 17$^{th}$ Ed. (1985). Often, intravenous compositions will comprise a solution of the liposomes suspended in an acceptable carrier, such as an aqueous carrier. Any of a variety of aqueous carriers can be used, e.g., water, buffered water, 0.4% saline, 0.9% isotonic saline, 0.3% glycine, 5% dextrose, and the like, and may include glycoproteins for enhanced stability, such as albumin, lipoprotein, globulin, etc. Often, normal buffered saline (135–150 mM NaCl) will be used. These compositions can be sterilized by conventional sterilization techniques, such as filtration. The compositions may contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, triethanolamine oleate, etc. These compositions can be sterilized using the techniques referred to above, or can be produced under sterile conditions. The concentration of liposomes in the carrier can vary. Generally, the concentration will be about 20–200 mg/mL, however persons of skill can vary the concentration to optimize treatment with different liposome components or for particular patients. For example, the concentration may be increased to lower the fluid load associated with treatment.

The amount of vinca alkaloids administered per dose is selected to be above the minimal therapeutic dose but below a toxic dose. The choice of amount per dose will depend on a number of factors, such as the medical history of the patient, the use of other therapies, and the nature of the disease. In certain embodiments, an initially low dose will be given, which can be increased based on the response and/or tolerance of the patient to the initial dose. For example, 0.5, 1.0, 1.5, 2.0, 2.4 $mg/m^2$ (i.e., mg vinca alkaloid, e.g. ,vincristine, per $m^2$ body surface area) or higher concentrations can be administered. In preferred embodiments, patients are administered a dose of 2.0 $mg/m^2$, corresponding to a lipid dose of about 40 $mg/m^2$ or about 1.1 mg/kg lipid and 0.05 mg/kg vincristine for an average 70 kg patient, or about 3 mg to about 6 mg vincristine per dose.

Patients typically will receive at least 2 courses of such treatment, and potentially more, depending on the response of the patient to the treatment. In single agent regimens, total courses of treatment are determined by the patient and physician based on observed responses and toxicity. Up to 12 courses of treatment, once every 14 days, have demonstrated satisfactory patient responses. Greater numbers may be warranted in certain cases. Similarly, the number of courses of treatment using lipo-CHOP will be determined by the patient and physician.

Because vincristine dosages are limited by neurotoxicity in humans, it is sometimes useful to co-administer liposomal vincristine with a treatment for neurotoxicity. This treatment may be prophylactic or therapeutic. An example is the administration of Neurontin™ gabapentin (Parke-Davis), or neurotonin, for treatment of neuropathic pain, e.g., 100–200 mg Neurontin™ is administered 3 times per day to an adult patient. If neuropathic pain improves, then liposomal vincristine treatments may continue. Because this type of prophylactic or therapeutic treatment is intended only to treat side-effects of liposomal vincristine, it is considered separately from the combination therapies set forth below.

This invention is based in part on the surprising discovery that, in contrast to free form vinca alkaloids, liposome-encapsulated vinca alkaloids can be administered without a cap on the total dosage. For example, whereas free form vincristine is typically administered with a cap of 2.0 mg, liposome-encapsulated vincristine can be administered at a constant dosage of, preferably, 2.0 $mg/m^2$. Thus, for a typical patient of from 1.5 to 3.0 $m^2$ surface area, a dose of from about 3.0 to about 6.0 mg vincristine can be administered.

X. Combination Therapies

In numerous embodiments, liposome-encapsulated vinca alkaloids will be administered in combination with one or more additional compounds or therapies. For example, multiple vinca alkaloids can be co-administered, or one or more vinca alkaloids can be administered in conjunction with another therapeutic compound, such as cyclophosphamide, doxorubicin, prednisone, other alkaloids such as the taxanes, camptothecins, and/or podophyllins, other chemotherapeutic agents such as antisense drugs or anti-tumor vaccines. In a preferred embodiment, liposome-encapsulated vincristine is co-administered with cyclophosphamide, doxorubicin, and prednisone. In certain embodiments, multiple compounds are loaded into the same liposomes. In other embodiments, liposome-encapsulated vinca alkaloids are formed individually and subsequently combined with other compounds for a single co-administration. Alternatively, certain therapies are administered sequentially in a predetermined order, such as in CHOP or lipo-CHOP. Liposome-encapsulated vincristine can also be formulated in a CVP combination, or cyclophosphamide-vincristine-prednisone.

Liposome-encapsulated vinca alkaloids can also be combined with anti-tumor agents such as monoclonal antibodies including, but not limited to, Oncolym™ (Techniclone Corp. Tustin, Calif.) or Rituxan™ (IDEC Pharmaceuticals), Bexxar™ (Coulter Pharmaceuticals, Palo Alto, Calif.), or IDEC-Y2B8 (IDEC Pharmaceuticals Corporation). In addition, liposome-encapsulated vinca alkaloids can be administered along with one or more non-molecular treatments such as radiation therapy, bone marrow transplantation, hormone therapy, surgery, etc.

In a preferred embodiment, liposome encapsulated vinca alkaloids are administered in combination with an anti-cancer compound or therapy which provides an increased or synergistic improvement in tumor reduction based on mechanism of action and non-overlapping toxicity profiles. In particular, liposomal vinca alkaloids can be delivered with a taxane, which optionally may also be a liposomal taxane. While it is thought that vinca alkaloids depolymerize microtubules and taxanes stabilize microtubules, the two compounds have been found to act synergistically in the impairment of tumor growth, presumably because both are involved in the inhibition of microtubule dynamics. See, Dumontet, C. and Sikic, B. I. (1999) *J Clin Onc.* 17(3) 1061–1070. Liposomal formulations of the vinca alkaloids according to the present invention will thus significantly diminish the myeloid and neurologic toxicity associated with the sequential administration of free form vinca alkaloids and taxanes.

Other combination therapies known to those of skill in the art can be used in conjunction with the methods of the present invention.

EXAMPLES

The following examples are offered to illustrate, but no to limit the claimed invention.

EXAMPLE 1

Making Liposome-Encapsulated Vincristine

Liposome-encapsulated vincristine (Vincristine Sulfate Liposome Injection) was prepared using a six vial kit. Vials 1 and 2 contained a vincristine sulfate solution (1 mg/mL Vincasar PFS® SP Pharmaceuticals LLC, Albuqueque, N.Mex.) in buffer comprising mannitol and sodium acetate, pH 4.5–4.7, vial 3 contained empty liposomes (100 mg/mL Sphingomyelin/Cholesterol liposomes, at a ratio of between about 60/40 to 50/50, or more preferably 55/45 mol %/mol %) in buffer comprising 300 mM citrate at pH 4.0, vials 4 and 5 contained an alkaline phosphate buffer (14.2 mg/mL dibasic sodium phosphate hepta hydrate), and vial 6 was an empty, sterile vial. The foregoing empty liposomes were prepared using thin film hydration and standard extrusion techniques, as described in U.S. Pat. No. 5,741,516.

4 mL of Vincristine Sulfate was removed from vials 1 and 2 and added to sterile vial 6. Subsequently, 0.8 mL sphingomyelin/cholesterol liposomes was removed from vial 3 and added to vial 6. Vial 6 was inverted five times to mix the materials. 20 mL of the sodium phosphate solution from vials 4 and 5 was added to vial 6. Vial 6 was again inverted five times, without shaking, to mix the materials. Vial 6 was then heated in a water bath at 60–65° C. for five minutes, after which the vial was again inverted five times. The vial was then again heated for five minutes and inverted five more times.

The final product contained 0.16 mg/mL vincristine sulfate and 3.2 mg/mL total lipid.

EXAMPLE 2

Liposome-Encapsulated Vincristine in Relapsed NHL Methods 50 patients with relapsed non-Hodgkin's Lymphoma (NHL), and 1 with Adult Lymphoblastic Lymphoma (ALL), were included in the study. Each patient was at least 16 years of age, did not have HIV or any other serious infection, did not have any disease of the central nervous system, and had normal renal function and neutrophils at least 0.5K, and platelets at least 50K. Each patient received up to 12 doses of 2.0 mg/m$^2$ of intravenous liposomal-vincristine administered once every 14 days. The liposomes used comprised sphingomyelin and cholesterol.

Results 35 of the 51 patients were evaluated. The median age of these 35 patients was 62 years (range 19–86), and 21 of the patients were male. 12 of the patients had follicular NHL, 7 had transformed, 11 diffuse large cell, 3 mantle cell, 1 NK cell, and one ALL. Clinical grade was high in 1, aggressive in 17, indolent in 10, and transformed in 7 patients. Serum LDH was high in 16 out of the 35 patients, and B2 microglobulin greater than 3.0 mg/L in 19 out of 30 patients. The median number of prior therapeutic regimens was 3 (range 1–10). 18 of the 35 patients were refractory to the regimen immediately preceding the liposome-encapsulated vincristine. All 35 had previously received vincristine administration. For the 34 patients with NHL, 14 patients exhibited a complete or partial response, for an overall response rate of 40% (95% confidence interval: 24%–58%). Responses according to clinical grade was as shown in Table 1.

|  | Indolent | Transformed | Aggressive | Transformed or Aggressive |
|---|---|---|---|---|
| # Patients | 10 | 7 | 17 | 24 |
| # Responders (complete or partial response) | 1 | 5 | 8 | 13 |
| % Complete or partial response | 10 | 71 | 47 | 54 |

-continued

|  | Indolent | Transformed | Aggressive | Transformed or Aggressive |
|---|---|---|---|---|
| 95% Confidence Interval | 1–45 | 29–96 | 23–72 | 33–74 |

Conclusions

Median response duration was 4 months. The fact that half of the responding patients maintain the response for at least 4 months after treatment is a surprising, unexpected and clinically impressive response for a heterogeneous group of patients who previously would have been given a very poor prognosis.

The above results demonstrate that full doses of liposomal vincristine can be given in relapsed NHL with good activity, even in heavily pretreated populations.

In addition, liposomal vincristine demonstrated significantly less non-specific toxicity than free vincristine. Peripheral neurotoxicity is the most frequent and dose-limiting toxic effect of free vincristine. Peripheral neuropathic effects usually begin in adults who receive a total dose of 5 to 6 mg (2–3 doses of free vincristine) and are generally significant after a cumulative dose of 15–20 mg (8–10 doses of free vincristine). Significantly, in the present study, a typical patient received 3–5 mg in one dose alone, and cumulative doses of up to 37 mg were delivered, with no patient reporting significant liposomal vincristine-induced peripheral neurotoxicity. Even higher total doses are likely to be tolerated. These higher doses are highly desirable for the management of NHL, and represent a significant and surprising step forward in the treatment of this disease.

EXAMPLE 3

Use of Liposomal Vinca Alkaloids as First-line Treatment for Lymphomas

This example illustrates the use of liposomal vinca alkaloids as a first-line treatment, in combination with other chemotherapeutics, for treatment of patients presenting with lymphomas, particularly non-Hodgkin's lymphoma (low-grade or intermediate-grade). Patients presenting with transformed or aggressive NHL may receive this improved combination treatment as a first-line treatment, or the physician may prefer single agent OncoTCS™ treatment as described in the previous examples. The combination therapy regimen set out below takes advantage of the surprising result that much higher doses of vincristine can be administered when delivered in the liposomes of the present invention, with greatly reduced toxicity.

The preferred combination regimen is an improved CHOP regime ("Lipo-CHOP") comprising: Cyclophosphamide, Hydroxydaunorubicin (doxorubicin), OncoTCS ™, and Prednisone. One treatment cycle takes about 5 days, and cycles are repeated about every 21–28 days. An exemplar cycle consists of Cyclophosphamide (750 mg/m$^2$ IV, d 1)

Hydroxydaunorubicin (50 mg/m$^2$ IV, d 1)

OncoTCS™ (2.0 mg/m$^2$ IV, d 1, (no cap necessary))

Prednisone (100 mg PO qd×5 day)

Treatments are conducted with the same nursing interventions required for standard CHOP treatment.

Patients receiving the improved CHOP treatment are expected to show significant improvement over standard CHOP in partial and complete remission rates, period of remission/time to relapse after treatment, and median survival times.

EXAMPLE 4

Treatment of lymphomas with single agent liposomal vincristine

In a further study, 50 human patients presenting with different classes of lymphoma were treated with single agent liposomal vincristine, as described in Example 2. Results were as indicated in the following chart:

|  | First Relapse from CR | Primary Refractory | Post-ABMT | ≧2 Relapses | Multicenter Study Population* |
|---|---|---|---|---|---|
| Number of Patients Evaluable | 11 | 11 | 10 | 26 | 36 |
| # CR | 4 | 0 | 0 | 0 | 0 |
| # PR | 4 | 0 | 2 | 10 | 12 |
| Overall Response Rate (%) | 73 | 0 | 20 | 38 | 33 |
| 95% Confidence Intervals (%) | 39 to 95 | 0 to 28 | 1 to 32 | 20 to 59 | |

18% grade 3 to 4 neurotoxicity; no toxic deaths.
CR = Complete response
PR = Partial response
Primary refractory means that no response to initial treatment was observed.
ABMT = Autologous bone marrow transplant Again, these results show that single agent treatment of liposomal vincristine is an excellent treatment for lymphomas. These results strongly suggest a role for liposomal vincristine in Lipo-CHOP and for single agent first line treatment of lymphomas.

EXAMPLE 5

Additional Studies

FIG. 1 provides results for a clinical trial using the herein-described methods, which demonstrates that the present methods are particularly effective in the treatment of indolent, transformed, relapsed, and aggressive post bone-marrow transplant (BMT) forms of non-Hodgkin's Lymphoma.

EXAMPLE 6

Response to Liposomal Vincristine per Prior Regimen Number

FIG. 2 provides results showing the number of evaluable patients with relapsed aggressive NHL, the number of such patients that exhibited a complete response or remission (CR), the number that exhibited a partial response or remission (PR), the percentage that exhibited either a CR or a PR, and the 95% confidence interval for each percentage value. These data are presented for patients who have received one prior treatment, two or more prior treatments, and, of the latter category, those who responded to the treatment immediately prior to the study and those who did not respond to the previous treatment.

This study demonstrates that the present methods are unusually effective for treating each category of patients.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a relapsed cancer in a human, said method comprising administering to said human a pharmaceutical composition comprising liposome-encapsulated vinctistine, wherein said relapsed cancer is a lymphoma or leukemia, and wherein said human has previously undergone at least one multi-agent combination regime.

2. The method of claim 1, wherein said relapsed cancer is a non-Hodgkin's Lymphoma.

3. The method of claim/wherein said non-Hodgkin's Lympho a is a member selected from the group consisting of low grade non-Hodgkin's Lymphoma, intermediate grade non-Hodgkin's Lymphoma, follicular lymphom, large cell lymphoma, B-cell lymphoma, T-celi lymphorna, Mantle cell lymphoma, Burkitt's lynphoma, NK cell lymphoma, and acute lymphoblastic lymphoma.

4. The method of claim 1, wherein said liposome comprises distearoylphosphatidylcholine.

5. The method of claim 4, wherein said liposome further comprises cholesterol.

6. The method of claim 1, wherein said liposome comprises sphingomyclin.

7. The method of claim 6, wherein said liposome further comprises cholesterol.

8. The method of claim 1, wherein said liposome comprises a pH gradient.

9. The method of claim 8, wherein the pH gradient is such that the pH is lower at the interior of said liposome than at the exterior of said liposome.

10. The method of claim 1, wherein said at least one multi-agent combination regime comprised administration of a free-form vinca-alkaloid.

11. The method of claim 10, wherein said free-form vinca alkaloid is a member selected from the group consisting of vincristine, vinblastine, vindesine, and vinorelbine.

12. The method of claim 1, wherein said at least one multi-agent combination regime comprised administration of an anffiacycline-containing combination regimen.

13. The method of claim 12, wherein said anthracycline is doxorubicin.

14. The method of claim 1, wherein said human has exhibited a partial response or a complete response to said multi-agent combination regime prior to the relapse of said cancer.

15. The method of claim 1, wherein said relapse is a second relapse.

16. The method of claim 1, wherein said liposome-encapsulated vincristine is administered systemically by intravenous delivery.

17. The method of claim 1, wherein said liposome-encapsulated vincristine is co-administered with at least one additional chemotherapeutic agent.

18. The method of claim 17, wherein said at least one additional chemotherapeutic agent is a member selected from the group consisting of cyclophosphamide, doxorubicin, prednisone, and combinations thereof.

19. The method of claim 1, wherein said liposome-encapsulated vincristine is co-administered with at least one additional anti-tumor agent.

20. The method of claim 19, wherein said additional anti-tumor agent is a monoclonal antibody.

21. The method of claim 20, wherein said monoclonal antibody is a member selected from the group consisting of Rituximab, iodine 131 (131I) Lym-1, and iodine 131 (131I) tositumomab.

22. The method of claim 19, wherein said additional anti-tumor agent is an antisense drug or an anti-tumor vaccine.

23. The method of claim 1, wherein said vincristine is administered at a dosage of between about 1.4 to about 2.4 mg/m2 to said human.

24. The method of claim 1, wherein said vincristine is administered to said patient once every 7–21 days.

25. The method of claim 24, wherein said vincristine is administered to said patient once every 14 days.

26. The method of claim 1, wherein said relapsed cancer is a lymphoma.

27. The method of claim 1, wherein said relapsed cancer is a leukemia.

* * * * *

UNITED STATES PATENT AND TRADEMARK OFFICE
CERTIFICATE OF CORRECTION

PATENT NO.    : 6,723,338 B1
DATED         : April 20, 2004
INVENTOR(S)   : Andreas H. Sarris et al.

It is certified that error appears in the above-identified patent and that said Letters Patent is hereby corrected as shown below:

<u>Title page,</u>
Item [56], References Cited, U.S. PATENT DOCUMENTS, the following should also be listed:
-- 5,714,163    02/03/1998    Forssen et al.
   5,814,335    09/29/1998    Webb et al.
   5,543,152    08/06/1996    Webb et al. --

<u>Column 20,</u>
Line 18, "claim/wherein" should read as -- claim 2, wherein --.
Line 19, "Lympho a" should read as -- Lymphoma --.
Line 22, "T-celi lymphorna" should read as -- T-cell lymphoma --.
Line 23, "lynphoma" should read as -- lymphoma --.
Line 30, "sphingomyclin" should read as -- sphingomyelin --.
Line 46, "anffiacycline" should read as -- anthracycline --.

Signed and Sealed this

Tenth Day of August, 2004

JON W. DUDAS
*Acting Director of the United States Patent and Trademark Office*